United States Patent

Kogi et al.

Patent Number: 5,270,304
Date of Patent: Dec. 14, 1993

[54] THERAPEUTIC 2-ALKYNYL ADENOSINE AGENT FOR ISCHEMIC DISEASES OF THE HEART OR BRAIN

[75] Inventors: Kentaro Kogi, Fukushima; Toichi Abiru, Sawara; Toyofumi Yamaguchi, Hachioji, all of Japan

[73] Assignees: Yamasa Shoyu Kabushiki Kaisha, Choshi; Toa Eiyo Ltd., Tokyo, both of Japan

[21] Appl. No.: 700,156

[22] PCT Filed: Nov. 15, 1989

[86] PCT No.: PCT/JP89/01158
§ 371 Date: May 15, 1991
§ 102(e) Date: May 15, 1991

[87] PCT Pub. No.: WO90/05526
PCT Pub. Date: May 31, 1990

[30] Foreign Application Priority Data

Nov. 15, 1988 [JP] Japan .................. 63-288513

[51] Int. Cl.$^5$ .............................. A61K 31/52
[52] U.S. Cl. .................. 514/46; 514/45; 536/27.6; 536/27.7
[58] Field of Search .......... 536/24, 26, 27.6, 27.7; 514/45, 46

[56] References Cited

U.S. PATENT DOCUMENTS 4,341,769  7/1982  Marumoto et al. ............. 514/46
4,880,783  11/1989  Mentzer et al. ............... 514/45
4,956,345  9/1990  Miyasaka et al. .............. 514/46

FOREIGN PATENT DOCUMENTS 0219876  4/1987  Japan ........................ 514/46

OTHER PUBLICATIONS

Nucleic Acids Research, Symposium Series, No. 12, 1983, pp. 5-8, Matsuda et al., "Introduction of Carbon Substituents at C-2 Position of Purine Nucleotides".

Nucleic Acids Research, Symposium Series, No. 16, 1985, pp. 97-100, Matsuda et al., "Synthesis and Pharmacological Activities of 2-alkynyl- and 2-alkenyl-adenine nucleosides".

Chem. Pharm. Bull., vol. 23, No. 4, 1975, pp. 759-775, Marumoto et al., "Synthesis and Coronary Vasodilating Activity of 2-substituted adenosines".

K. J. Isselbacher et al., "Harrison's Principles of Internal Medicine", chapter 250 Ninth edition, 1980, pp. 1156-1166, Atherosclerosis and Other Forms of Arteriosclerosis.

Matsuda et al., Chem. Pharm. Bull. vol. 33, No. 4. pp. 1766-1769 (1985).

The Merck Manual of Diagnosis and Therapy, pp. 1382-1383, (1987).

Primary Examiner—Johnnie R. Brown
Assistant Examiner—James O. Wilson
Attorney, Agent, or Firm—Wenderoth, Lind & Ponack

[57] ABSTRACT

The present invention concerns a therapeutic-prophylactic agent for ischemic diseases of the heart or brain, comprising as an active ingredient a 2-alkynyladenosine represented by the following formula:

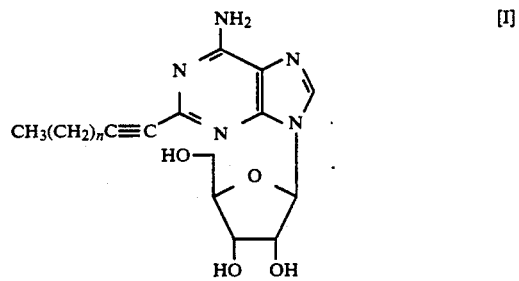

wherein n represents an integer of from 2 to 15.

3 Claims, No Drawings

THERAPEUTIC 2-ALKYNYL ADENOSINE AGENT FOR ISCHEMIC DISEASES OF THE HEART OR BRAIN

FIELD OF THE INVENTION

The present invention relates to a therapeutic-prophylactic agent for ischemic diseases of the heart or brain comprising a 2-alkynyladenosine as an active ingredient.

BACKGROUND OF THE INVENTION

Adenosine, which is a physiologically active substance in vivo, has a variety of physiological activities and has been known to play an important role in tissue cells or nerve functions, leading to homeostasis maintenance. However, adenosine given externally will be deaminated by adenosine deaminase so rapidly that it will immediately be inactivated.

Owing to such reasons as mentioned above, various attempts have been made hitherto to synthesize adenosine derivatives for the purposes of ameliorating pharmacological activity, imparting adenosine deaminase resistance, alleviating side-effects, etc., and further attempts to develop them as pharmaceutical products have been actively made. Among them, various 2-substituted adenosine derivatives have been synthesized. For example, as typically represented by 2-methoxyphenyladenosine (Hirata, M., Kawazoe, K., Tanabe, M. and Kikuchi, K.: Japan J. Pharmacol., 27, 689 (1977)) or 2-phenylaminoadenosine (Marumoto, R., Yoshioka, Y., Miyashita, O., Shima, S., Imai, K., Kawazoe, K. and Honjo, M.: Chem. Pharm. Bull., 23, 759 (1975)), those exhibiting physiological activities such as adenosine deaminase inhibitory effect, coronary vasodilating effect, platelet aggregation inhibitory effect, antiviral effect, etc. have been obtained.

Since adenosine has a potent vasodilating effect as well as a potent platelet aggregation inhibitory effect, there have been hitherto synthesized various adenosine derivatives including the above-mentioned derivatives for the purposes of remedying ischemic heart diseases, ischemic brain diseases, etc. However, the adenosine derivatives of the prior art still cannot be free from such side-effects as adenosine has, such as atrioventricular conduction inhibitory effect, reduction of renal blood flow amount, etc., and no excellent compounds have been found as yet.

On the other hand, a 2-alkynyladenosine having a substituent introduced by carbon-carbon bond at the 2-position of adenosine is disclosed in Japanese laid-open patent publications [Japanese Laid-Open Patent Publications Nos. 99395/1987 and 99330/1987]. However, only its use as an antihypertensive agent is described in these publications, and no other pharmacological effects, particularly ameliorating effects for ischemic diseases such as platelet aggregation inhibitory effect, coronary blood flow increasing effect, cerebral blood flow increasing effect, and brain protecting effect (e.g. anti-hypoxia effect and anti-anoxia effect), are referred to therein.

Generally speaking, drugs to be used for therapy and/or prophylaxis of ischemic heart diseases such as angina pectoris, heart failure, myocardial infarction, etc., as well as ischemic cerebral diseases such as cerebral circulatory disorders should desirably be compounds having platelet aggregation inhibitory effect and blood flow increasing effect or brain protecting effect at the lesion site. Therefore, in the therapy for ischemic diseases of the heart or brain, it would be of great significance to provide an adenosine derivative having a potent platelet aggregation inhibitory effect, coronary blood flow increasing effect, cerebral blood flow increasing effect or brain protecting effect without entailing side-effects as mentioned above.

SUMMARY OF THE INVENTION

We have investigated 2-alkynyladenosines for their blood flow increasing effects on various blood vessels such as coronary artery, vertebral artery, etc., platelet aggregation inhibitory effect and brain protecting effect under hypoxia or anoxia. Further, from the standpoint of side-effects, we have conducted intensive studies on the appearance of atrioventricular block in the heart and the reduction of renal blood flow amount. As a result, we have found that the compounds represented by the following formula [I] have a potent platelet aggregation inhibitory effect, potent blood flow increasing effects on various blood vessels and a potent brain protecting effect in combination, and yet they do not practically cause the appearance of atrioventricular block or the reduction of renal blood flow amount which are side-effects associated with adenosine and adenosine derivatives known in the art and rather exhibit excellent characteristics for prophylaxis and/or therapy for various ischemic diseases such as ischemic heart disease and ischemic brain disease, and we have eventually accomplished the present invention.

More specifically, the present invention provides a therapeutic-prophylactic agent for ischemic diseases of the heart or brain comprising as an active ingredient a 2-alkynyladenosine represented by the formula [I]:

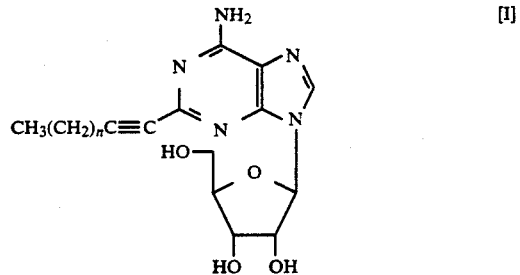

wherein n represents an integer of from 2 to 15.

The present invention also provides a therapeutic-prophylactic agent for ischemic diseases of the heart or brain comprising a safe and effective amount of a 2-alkynyladenosine represented by the formula [I] as mentioned above and a pharmaceutically acceptable carrier.

Further, the present invention provides a therapeutic or prophylactic method for an ischemic disease of the heart or brain in mammals suffering therefrom which comprises administering to such mammals a safe and effective amount of a 2-alkynyladenosine as mentioned above.

The present invention, still further, concerns the use of the above-mentioned 2-alkynyladenosine for the manufacture of a therapeutic-prophylactic agent for ischemic diseases of the heart or brain.

DESCRIPTION OF THE PREFERRED EMBODIMENTS

For the 2-alkynyladenosines represented by the formula [I], those with n in the range of from 2 to 13, more preferably from 3 to 7, should preferably be used as the active ingredients in view of the biological activities as described hereinafter.

The 2-alkynyladenosines which are the active ingredients of the drug of the present invention (hereinafter referred to as "the compounds of the present invention") can be synthesized by reacting a 2-halogenoadenosine represented by the formula [II]:

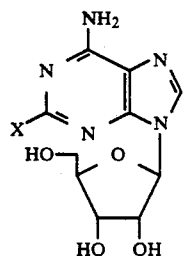

wherein X represents iodine or bromine, with an alkyne represented by the formula [III]:

$CH \equiv C(CH_2)_n CH_3$     [III]

wherein n represents an integer of from 2 to 15, in a solvent in the presence of bis(triphenylphosphine) palladium dichloride and cuprous iodide (see Japanese Laid-Open Patent Publications Nos. 99330/1987 and 99395/1987).

The alkyne used in the reaction should be chosen to have the number of n corresponding to the desired compound of the present invention.

For the reaction solvent, a basic solvent can be employed, for example, a solvent mixture of triethylamine and N,N-dimethylformamide. In place of triethylamine, tertiary amines such as tributylamine, trioctylamine, N,N,N'-N'-tetramethyl-1,8-naphthalenediamine, dimethylaniline, diethylaniline, pyridine, etc. can be used, and in place of N,N-dimethylformamide, aprotic polar solvents such as N,N-dimethylacetamide, dimethyl sulfoxide, and acetonitrile can be used.

The reaction terminates in several hours at room temperature to solvent reflux temperature.

The compounds of the present invention can be isolated by any conventional separation and purification method. For example, adsorption chromatography, ionexchange chromatography, extraction or recrystallization can be applied for the isolation.

The drugs of the present invention can be used for the purposes of prophylaxis and/or therapy of ischemic heart diseases such as angina pectoris, heart failure and myocardial infarction; or ischemic cerebral diseases such as cerebral circulatory disorders due to cerebral infarction sequelae or cerebral hemorrhage sequelae, acute cerebral ischemia due to hypoxia or anoxia in the brain, etc.

When the compounds of the present invention are utilized as drugs, the compounds of the present invention are used in their free forms or as acid addition salts with pharmaceutically acceptable acids. Examples of such acid addition salts are inorganic acid salts such as hydrochloride, sulfate and hydrobromide, or organic acid salts such as oxalate, citrate and malate.

The compounds of the present invention can also be administered orally or parenterally together with conventional pharmaceutically acceptable carriers for therapy and/or prophylaxis.

The drugs suitable for oral administration can be solid form preparations such as powders, granules, capsules and tablets, or liquid form preparations such as syrups and elixirs. The drugs suitable for parenteral administration can be injections, suppositories, ointments, or inhalants. These preparations can be prepared by a conventional method by adding pharmaceutically acceptable carriers to the compounds of the present invention. Further, according to the known technique, they can also be formed into sustained release preparations.

In the preparation of the solid form preparation for oral administration, the compound of the present invention is mixed with an excipient such as lactose, starch, crystalline cellulose, calcium lactate, calcium monohydrogenphosphate, magnesium aluminometasilicate or anhydrous silicic acid to give powders, or, if necessary, the powder is further mixed with a binding agent such as refined sugar, hydroxypropylcellulose or polyvinylpyrrolidone, or a disintegrating agent such as carboxymethylcellulose or carboxymethylcellulose calcium for wet or dry granulation to give granules. In the preparation of tablets, these powders and granules, if necessary, mixed with a lubricant such as magnesium stearate or talc may be punched into tablets. Alternatively, these granules or tablets can be coated with an enteric base such as hydroxypropylmethylcellulose phthalate or a methyl methacrylate copolymer to give enteric-coated preparations, or they can be coated with ethylcellulose, carnauba wax or a hydrogenated oil to give sustained release preparations. Further, in order to prepare capsules, the powders or granules can be charged into hard capsules, or the compound of the present invention is first dissolved in glycerol, polyethylene glycol, sesame oil or olive oil and then coated with a gelatin film to give soft capsules.

In order to prepare the liquid preparation for oral administration, the compound of the present invention and a sweetener such as refined sugar, sorbitol or glycerol may be dissolved in water to give a clear syrup, or the syrup may be further mixed with an essential oil or ethanol to give an elixir, or with gum arabic, tragacanth gum, polysorbate 80 or carboxymethylcellulose sodium to give an emulsion or a suspension. These liquid preparations may also contain flavoring agents, colorants, preservatives, etc., if desired.

In order to prepare the injection, the compound of the present invention may be dissolved in distilled water for injection, if necessary, together with a pH adjusting acid, sodium lactate, sodium monohydrogenphosphate or sodium dihydrogenphosphate, and an isotonizing agent such as sodium chloride or glucose, aseptically filtered and charged into ampoules, or the solution may be mixed with mannitol, dextrin, cyclodextrin or gelatin and lyophilized under vacuum to give an injection which should be dissolved on use. Furthermore, the compound of the present invention can be mixed with lecithin, polysorbate 80 or polyoxyethylene-hydrogenated castor oil, and the mixture is emulsified in water to give an emulsion for injection.

In order to prepare the preparation for rectal administration, the compound of the present invention may be melted by heating together with a suppository base such as a tri-, di- or mono-glyceride of cacao fatty acid or polyethylene glycol, poured into a mold and cooled, or the compound of the present invention may be dissolved into polyethylene glycol or soybean oil and then coated with a gelatin film.

In order to prepare the preparation for external application, the compound of the present invention is added to white vaseline, beeswax, liquid paraffin or polyethylene glycol and the mixture is kneaded, if necessary, under heat to give an ointment, or it is kneaded with an adhesive such as rosin or an alkyl acrylate polymer, and then spread over a nonwoven fabric made of, for example, polyethylene to give a tape preparation.

In order to prepare the inhalant, the compound of the present invention is dissolved or dispersed in a propellant such as flon gas and charged into a pressure vessel to give an aerosol.

The dose of the compound of the present invention depends on the age, body weight and the conditions of disease but is generally about 0.1 mg to 100 mg per day per individual and administered desirably in one portion or several portions.

Synthesis example of the compound of the present invention 6.0 g of 6-chloro-2-iodo-9-(2,3,5-tri-O-acetyl-$\beta$-D-ribofuranosyl)purine was added to 60 ml of methanol/ammonia (saturated at 0° C.) to cause reaction at a temperature of 60° C. for 17 hours in a sealed tube. The reaction solution was cooled, then degassed, and concentrated under reduced pressure. Crystallization of the residue from water afforded 3.94 g of 2-iodoadenosine (90% yield).

Melting point: 141° to 144° C.

393 mg (1 mmole) of the 2-iodoadenosine was dissolved in dimethylformamide (10 ml) - triethylamine (3 ml), and to the solution obtained were added 21 mg of bis(triphenylphosphine) palladium dichloride and 12 mg of cuprous iodide. To the resulting solution was added an alkyne (1.1 equivalent) in an argon stream, and the mixture was stirred under heat at 80° C. After the reaction solution was concentrated under reduced pressure, the residue was dissolved in methanol, and hydrogen sulfide was passed through the solution for one minute. The precipitate formed was filtered off, and the filtrate was concentrated to dryness under reduced pressure. The residue was purified by column chromatography on silica gel and recrystallized from methanol or methanol-water to obtain 2-alkynyladenosine. The reaction time, yield, melting point and infrared absorption spectrum are shown in TABLE 1.

TABLE 1

| Compound No. | Species of Alkynyl Group | Reaction Time (hr) | Yield (%) | Melting Point (°C.) | IR (KBr) cm$^{-1}$ $\nu$C≡C |
|---|---|---|---|---|---|
| 1 | —C≡C(CH$_2$)$_2$CH$_3$ | 1 | 90 | 129–132 | 2230 |
| 2 | —C≡C(CH$_2$)$_3$CH$_3$ | 1 | 85 | 121–125 | 2230 |
| 3 | —C≡C(CH$_2$)$_4$CH$_3$ | 1 | 93 | 113–115 | 2230 |
| 4 | —C≡C(CH$_2$)$_5$CH$_3$ | 1 | 84 | 101–103 | 2230 |
| 5 | —C≡C(CH$_2$)$_6$CH$_3$ | 1 | 90 | 98–101 | 2230 |
| 6 | —C≡C(CH$_2$)$_7$CH$_3$ | 1 | 88 | 121–123 | 2230 |
| 7 | —C≡C(CH$_2$)$_8$CH$_3$ | — | — | — | — |
| 8 | —C≡C(CH$_2$)$_9$CH$_3$ | 1 | 97 | 128–130 | 2230 |
| 9 | —C≡C(CH$_2$)$_{10}$CH$_3$ | — | — | — | — |
| 10 | —C≡C(CH$_2$)$_{11}$CH$_3$ | 1 | 93 | 131–134 | 2230 |
| 11 | —C≡C(CH$_2$)$_{12}$CH$_3$ | — | — | — | — |
| 12 | —C≡C(CH$_2$)$_{13}$CH$_3$ | 3 | 98 | 134–136 | 2230 |
| 13 | —C≡C(CH$_2$)$_{14}$CH$_3$ | 24 | 80 | 138–139 | 2230 |
| 14 | —C≡C(CH$_2$)$_{15}$CH$_3$ | 24 | 72 | 131–134 | 2230 |

Pharmacological test examples

Test Example 1

Platelet aggregation inhibitory effect

Male Nippon white rabbits weighing 2.0 to 2.5 kg were used.

Under anesthesia with pentobarbital sodium, blood was sampled from common carotid artery, and mixed with 1/7 volume of a citric acid dextrose solution which is an anticoagulant. Next, centrifugation was carried out at 140×g for 15 minutes, and the supernatant (platelet-enriched plasma: PRP) was collected. The PRP was centrifuged at 1300×g for 7 minutes. The platelet pellets obtained were washed with a HEPES buffer for platelet washing (pH 6.5) and centrifuged at 1300×g for 7 minutes. The platelet pellets washed twice under the same conditions were suspended in a suspending solution (a buffer for platelet washing to which 1.0% human fibrinogen, 1.8 mM calcium chloride, 1.2 mM magnesium chloride were added) to prepare a platelet suspension to to 5 to 8×10$^8$ platelets/ml.

For assaying platelet aggregation ability, an aggregometer was used, and 10 $\mu$l of a test drug was added to 380 $\mu$l of the platelet suspension. Three minutes later, 10 $\mu$l of a platelet aggregating substance (10 $\mu$M adenosine 5'-diphosphate at a final concentration) was added thereto to induce aggregation.

The platelet aggregation inhibitory effect by the test drug is represented by the IC$_{50}$ value (concentration of the test drug which inhibits 50% of platelet aggregation). The results are shown in column (A) in TABLE 2.

Test Example 2

Coronary artery blood flow increasing effect

Adult mongrel dogs weighing 9 to 15 kg were anesthetized with pentobarbital sodium, and the chest of each was opened under artificial respiration. After pericardium excision, the left anterior descending coronary artery was peeled off from the surrounding tissues, a probe for blood flow measurement was set under heparin sodium treatment, and the coronary blood flow was measured by the use of an electromagnetic blood flow meter.

The test drug was injected intraarterially into the coronary artery. The coronary artery blood flow increasing effect is represented by the ED$_{50}$ value (dosage when blood flow is increased by 50% by administration of the test drug when, after blocking the coronary blood flow for 15 seconds, the amount of the blood flow increased by the reactive hyperemia occurring when de-blocked is defined as 100%). The results are shown in column (B) in TABLE 2.

Test Example 3

Vertebral artery blood flow increasing effect

The chests of female and male adult mongrel dogs weighing 8 to 13 kg, under anesthesia by intravenous administration of pentobarbital sodium, were opened under artificial respiration along the median line to expose the left vertebral artery. Under heparin sodium treatment, a polyethylene cannula was inserted into the left vertebral artery. A probe for blood flow measurement was set at the other end of the cannula, and a tube for blood perfusion led from the left femoral artery was connected to the probe. The vertebral artery blood flow was measured by means of an electromagnetic blood flow meter.

The test drug was injected intraarterially into the vertebral artery. The vertebral artery blood flow increasing effect is represented by the $ED_{50}$ value (dosage when blood flow is increased by 50% by administration of the test drug when the amount of the blood flow increased by vertebral administration of 100 μg/kg papaverine hydrochloride (exhibiting substantially the maximum reaction) is defined as 100%). The results are shown in column (C) in TABLE 2.

TABLE 2

| (A) Platelet Aggregation Inhibitory Effect | | |
|---|---|---|
| Compound No. | Species of Alkynyl Group | $IC_{50}$ (M) |
| 2 | —C≡C(CH$_2$)$_3$CH$_3$ | $6.1 \times 10^{-8}$ |
| 4 | —C≡C(CH$_2$)$_5$CH$_3$ | $1.4 \times 10^{-7}$ |
| 5 | —C≡C(CH$_2$)$_6$CH$_3$ | $2.1 \times 10^{-7}$ |
| 6 | —C≡C(CH$_2$)$_7$CH$_3$ | $7.2 \times 10^{-7}$ |
| 12 | —C≡C(CH$_2$)$_{13}$CH$_3$ | $3.1 \times 10^{-6}<$ |
| Adenosine | Control | $3.2 \times 10^{-6}$ |

| Compound No. | Species of Alkynyl Group | $ED_{50}$ (μg/kg) |
|---|---|---|
| (B) Coronary Artery Blood Flow Increasing Effect | | |
| 2 | —C≡C(CH$_2$)$_3$CH$_3$ | 0.002 |
| 4 | —C≡C(CH$_2$)$_5$CH$_3$ | 0.008 |
| 5 | —C≡C(CH$_2$)$_6$CH$_3$ | 0.075 |
| 6 | —C≡C(CH$_2$)$_7$CH$_3$ | 0.15 |
| 12 | —C≡C(CH$_2$)$_{13}$CH$_3$ | 0.1< |
| Adenosine | Control | 0.1 |
| (C) Vertebral Artery Blood Flow Increasing Effect | | |
| 2 | —C≡C(CH$_2$)$_3$CH$_3$ | 0.14 |
| 4 | —C≡C(CH$_2$)$_5$CH$_3$ | 0.4 |
| 5 | —C≡C(CH$_2$)$_6$CH$_3$ | 1.2 |
| 6 | —C≡C(CH$_2$)$_7$CH$_3$ | 3< |
| 12 | —C≡C(CH$_2$)$_{13}$CH$_3$ | 3< |
| Adenosine | Control | 0.52 |

Test Example 4

Brain protecting effect under hypoxia or anoxia

When the brain falls into hypoxia by cerebral circulatory disorder, its function will be rapidly and irreversibly lost. Accordingly, the pharmacological activities of the drugs were evaluated with the extension time relative to the survival time of the test animals under hypoxia or anoxia induced by changing gas phase components or by a drug.

Experiment 1

Normobaric hypoxia method

Evaluation of the pharmacological activity by the normobaric hypoxia method was conducted by following the method of Yasuda et al. (Arch. Int. Pharmacodyn, 233, 136–144 (1978)) as described below.

Animals used were 8 to 11 male ICR mice of 7 weeks age (Clea Japan) per group.

The mice were placed in a desiccator made of glass, and hypoxia was induced by passing a gas mixture of 96% $N_2$ and 4% $O_2$ at a flow rate of 5 liters/min. The time after the passing of the gas into the desiccator to the respiration arrest of each mouse was measured and defined as the survival time.

The test drug was administered intraperitoneally 30 minutes before the initiation of gas passing. The average survival times for the control group and the group to which the test drug was administered were calculated. The results are shown in column (A) in TABLE 3.

The test drug was suspended in a physiological saline containing 0.5% CMC (carboxymethyl cellulose), and the dosage was 0.1 ml per 10 g of body weight. To the mice of the control group was administered 0.5% of the CMC physiological saline in the same manner. The statistical analysis was conducted according to the student's t-test.

Results

Significant extension of survival time was recognized for 2-hexynyladenosine (Compound 2) by the administration of 1 mg/kg, and for 2-octynyladenosine (Compound 4) by the administration of 1 mg/kg and 3 mg/kg.

Experiment 2

Potassium cyanide (KCN)-induced anoxia method

Evaluation of the pharmacological activity by the KCN-induced anoxia method was conducted according to the Karasawa et al. procedure (J. Pharmacobio-Dyn. 5, 295–300 (1982)).

Animals used were 13 to 15 male ICR mice of 8 weeks age (Clea Japan) per group.

The test drug was administered intraperitoneally at a dose of 0.1 ml per 10 g of body weight, and 30 minutes later, 2.5 mg/kg of KCN was administered rapidly into a tail vein. The survival time was measured. The test drug was prepared in the same manner as in Experiment 1.

The average survival times for the control group and the group to which the test drug was administered were calculated. The results are shown in column (B) in TABLE 3. The mice which exhibited no respiration arrest over 180 seconds or longer after KCN administration were rated as survival examples, and the survival time was calculated as 180 seconds in calculating the average survival time.

Results

By the administration of 1 mg/kg of 2-hexynyladenosine (Compound 2) and 30 mg/kg of 2-hexadecynyladenosine (Compound 12), significant extension effects were exhibited as compared with the survival times of the respective control groups.

TABLE 3

| Compound No. | Species of Alkynyl Group | Dose (mg/kg) | Number of Test Animal | Average Survival Time (sec.) |
|---|---|---|---|---|
| (A) Normobaric Hypoxia Method | | | | |
| 2 | —C≡C(CH$_2$)$_3$CH$_3$ | 0.1 | 9 | 171.9 (±22.1)[a] |
| | | 0.3 | 9 | 169.2 (±23.5) |
| | | 1.0 | 9 | 217.3 (±26.2)** |
| 4 | —C≡C(CH$_2$)$_5$CH$_3$ | 0.3 | 9 | 128.7 (±4.8) |
| | | 1.0 | 9 | 222.9 (±25.9)** |
| | | 3.0 | 9 | 230.6 (±26.7)** |
| Control | — | — | 11 | (126.8 ±10.7) |
| (B) Potassium Cyanide Induced Anoxia Method | | | | |
| 2 | —C≡C(CH$_2$)$_3$CH$_3$ | 1.0 | 15 | 50.05 (±3.8)* |
| Control (1) | — | — | 15 | 39.8 (±2.4) |
| 12 | —C≡C(CH$_2$)$_{13}$CH$_3$ | 30 | 15 | 76.7 (±11.7)* |
| Control | — | — | 13 | 41.8 (±1.9) |

TABLE 3-continued

| Compound No. | Species of Alkynyl Group | Dose (mg/kg) | Number of Test Animal | Average Survival Time (sec.) |
|---|---|---|---|---|
| (2) | | | | | a) Standard error in brackets (S.E.)
**P < 0.01
*P < 0.05

Test Example 5

Effect on renal blood flow

Female and male adult mongrel dogs weighing 10 to 15 kg were used. After each dog was anesthetized by intravenous administration of 30 mg/kg of pentobarbital sodium, it was fixed on the back, and the left lower abdominal portion was cut open under artificial respiration to expose the left renal artery. Under heparin sodium treatment, a polyethylene cannula was inserted into the renal artery, and at the other end of the cannula was set a probe for blood flow measurement. Self-perfusion was effected by means of a tube for blood perfusion led from the left femoral artery and connected to the probe, and the renal artery blood flow was measured by means of an electromagnetic blood flow meter.

The test drug was injected intraarterially into the renal artery. The renal blood flow reduction effect is represented by the $ID_{50}$ value (dosage when blood flow is reduced by 50% by the test drug administration). The results are shown in column (A) in TABLE 4.

Test Example 6

Effect on atrioventricular conduction

Each of male guinea pigs weighing 360 to 600 g, after being anesthetized by intraperitoneal administration of 1.4 g/kg of urethane, was fixed on the back, and the trachea was cut open for ensuring airway, a polyethylene tube being inserted thereinto. The blood pressure was measured through a carrier amplifier by connecting the cannula inserted into the left common carotid artery to a pressure transducer. The electrocardiogram was recorded by means of a bioelectric amplifier according to the second induction method, and the PQ interval was measured from the electrocardiogram.

The test drug was administered through the left femoral vein, and the presence or absence of appearance of atrioventricular block is represented by the appearance ratio of the second degree of atrioventricular block (number of animals showing appearance/number of animals used) by the test drug administration. The results are shown in column (B) in TABLE 4.

TABLE 4

| (A) Renal Blood Flow Reduction Effect | | |
|---|---|---|
| Compound No. | Species of Alkynyl Group | $ID_{50}$ (μg/kg) |
| 2 | —C≡C(CH$_2$)$_3$CH$_3$ | 0.15 |
| 4 | —C≡C(CH$_2$)$_5$CH$_3$ | 3< |
| 5 | —C≡C(CH$_2$)$_6$CH$_3$ | 3< |
| 6 | —C≡C(CH$_2$)$_7$CH$_3$ | 3< |
| 12 | —C≡C(CH$_2$)$_{13}$CH$_3$ | 3< |
| Adenosine | Control | 0.2 |

| (B) Atrioventricular Block Appearance Ratio | | |
|---|---|---|
| Compound No. | Species of Alkynyl Group | *Number of Animals Showing Appearance/Number of Animals Used |
| 2 | —C≡C(CH$_2$)$_3$CH$_3$ | 6/6 |
| 4 | —C≡C(CH$_2$)$_5$CH$_3$ | 1/6 |
| 5 | —C≡C(CH$_2$)$_6$CH$_3$ | 0/6 |

TABLE 4-continued

| 6 | —C≡C(CH$_2$)$_7$CH$_3$ | 1/6 |
|---|---|---|
| 12 | —C≡C(CH$_2$)$_{13}$CH$_3$ | 0/6 |
| Adenosine | Control | 6/6 |

*After intravenous administration of 300 μg/kg

Test Example 7

Acute toxicity

By the use of Slc:ICR mice (7 to 8 weeks old), the acute toxicity tests of Compound 4 (n=5) and Compound 12 (n=13) were conducted. For all of the compounds, no lethal case was recognized by oral administration of the pharmaceutically and physically acceptable maximum amount of 1000 mg/kg, and the $LD_{50}$ value was estimated to be 1000 mg/kg or higher in each case.

Example of preparation formulation

Example 1

| Compound (6) | 25 mg |
|---|---|
| Potato starch | 150 mg |
| Soft silicic acid anhydride | 50 mg |
| Magnesium stearate | 10 mg |
| Lactose | 765 mg |
| Total: | 1000 mg |

The above components were uniformly mixed and placed into hard capsules each in an amount of 200 mg.

Example 2

| Compound (4) | 25 mg |
|---|---|
| Potato starch | 150 mg |
| Crystalline cellulose | 60 mg |
| Soft silicic acid anhydride | 50 mg |
| Hydroxypropyl cellulose | 30 mg |
| Magnesium stearate | 15 mg |
| Lactose | 670 mg |
| Total: | 1000 mg |

Compound (4), lactose, potato starch, crystalline cellulose and soft silica acid anhydride were mixed, and 10% methanolic solution of hydroxypropyl cellulose was added. The mixture was granulated by kneading and then extruded through a screen with a diameter of 0.8 mm to prepare granules. After drying, magnesium stearate was added, and the mixture was compression molded into tablets each of 200 mg.

Example 3

| Compound (2) | 25 mg |
|---|---|
| Propylene glycol | Total: 10 ml |

Compound (2) was dissolved in propylene glycol, and the solution was aseptically filtered and then placed into ampoules each in an amount of 0.2 ml.

Example 4

| Compound (5) | 25 mg |
|---|---|
| Polyethylene glycol 1500 | 3000 mg |
| Polyethylene glycol 6000 | 1975 mg |
| Total: | 5000 mg |

The above components were mixed uniformly by heating and melting at 60° C. The mixture was cast into a plastic mold and then cooled to form a suppository of 1 g.

As described above, the 2-alkynyladenosine, which is the active ingredient of the drug of the present invention, has a remarkable platelet aggregation inhibitory effect, blood flow increasing effect of various blood vessels (coronary artery and vertebral artery) and brain protecting effect in combination. It further has weak side-effects such as appearance of atrioventricular block in myocardium and reduction effect of renal blood flow, possessed by adenosine or adenosine derivatives known in the art, thus overcoming the drawbacks of the prior art. To describe in more detail, the 2-alkynyladenosine, which is the active ingredient of the present drug, has an extremely high ratio of the primary effects such as platelet aggregation inhibitory effect, blood flow increasing effect of various blood vessels, and brain protecting effect to the side-effects such as atrioventricular block appearance ratio and renal blood flow reduction effect, that is, the 2-alkynyladenosine has an extremely broad margin of safety as compared to the prior compounds. For example, the margins of safety (coefficients) of the 2-alkynyladenosine calculated on the basis of the results in TABLE 2 and TABLE 4 by taking an example of coronary artery blood flow increasing effect as the primary effect and renal blood flow reduction effect as the side-effect are as shown below in TABLE 5. From TABLE 5, it can be understood that the 2-alkynyladenosine is a compound having a broader margin of safety as compared with adenosine.

TABLE 5

| Compound No. | Species of Alkynyl Group | Safety Coefficient |
| --- | --- | --- |
| 2 | $-C\equiv C(CH_2)_3CH_3$ | 75 |
| 4 | $-C\equiv C(CH_2)_5CH_3$ | 375< |
| 5 | $-C\equiv C(CH_2)_6CH_3$ | 40< |
| 6 | $-C\equiv C(CH_2)_7CH_3$ | 20< |
| 12 | $-C\equiv C(CH_2)_{13}CH_3$ | 30 |
| Adenosine | Control | 2 |

Although it can be seen from TABLE 2 and TABLE 4 that the 2-alkynyladenosine is equal to or higher than adenosine in the primary effects, the atrioventricular block appearance ratio which is one of the side-effects is suppressed at a low level. In this connection, Compound No. 2 has the same atrioventricular block appearance ratio as that of adenosine which is the control drug, but this has been brought about by administration of a dose as large as 300 μg/kg (intravenous administration), and in view of the strength of the primary effects of said compound, it may be considered that the atrioventricular block appearance can be suppressed when this compound is administered in an effective amount for activity appearance of the primary effects.

INDUSTRIAL APPLICABILITY

According to the present invention, it has become possible for the first time to provide a drug which is extremely excellent and significant for prophylaxis and/or therapy of ischemic heart diseases such as angina pectoris, heart failure, myocardial infarction, etc. and ischemic cerebral diseases such as cerebral circulatory disorders due to cerebral infarction sequelae or cerebral hemorrhage sequelae.

What is claimed is:

1. A therapeutic method for treating an ischemic disease of the heart or brain in mammals suffering therefrom which comprises administering to such mammals a safe and effective ischemic disease treating amount of a 2-alkynyladenosine represented by the following formula:

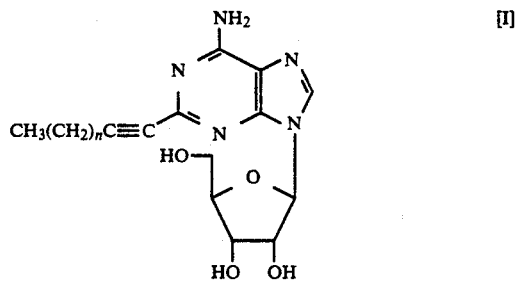

wherein n represents an integer of from 2 to 15.

2. The therapeutic method according to claim 1, wherein n is within the range of from 2 to 13.

3. The therapeutic method according to claim 1, wherein n is within the range of from 3 to 7.